(12) United States Patent
Rigg et al.

(10) Patent No.: US 11,679,068 B2
(45) Date of Patent: Jun. 20, 2023

(54) HYDROXY CINNAMATE AND SILANOL ADDUCT COATED INORGANIC SUNSCREEN AGENTS

(71) Applicant: VIZOR, LLC, Middlesex, NJ (US)

(72) Inventors: Yannick Rigg, Springfield Gardens, NY (US); Richard Rigg, Richmond Hills, NY (US)

(73) Assignee: VIZOR, LLC, Middlesex, NJ (US)

( * ) Notice: Subject to any disclaimer, the term of this patent is extended or adjusted under 35 U.S.C. 154(b) by 256 days.

(21) Appl. No.: 16/638,175

(22) PCT Filed: Aug. 31, 2018

(86) PCT No.: PCT/US2018/049035
§ 371 (c)(1),
(2) Date: Feb. 11, 2020

(87) PCT Pub. No.: WO2019/050788
PCT Pub. Date: Mar. 14, 2019

(65) Prior Publication Data
US 2021/0369576 A1 Dec. 2, 2021

Related U.S. Application Data

(60) Provisional application No. 62/554,069, filed on Sep. 5, 2017.

(51) Int. Cl.
| | | |
|---|---|---|
| *A61K 8/29* | (2006.01) | |
| *A61K 8/02* | (2006.01) | |
| *A61K 8/27* | (2006.01) | |
| *A61K 8/365* | (2006.01) | |
| *A61K 8/58* | (2006.01) | |
| *A61Q 17/04* | (2006.01) | |

(52) U.S. Cl.
CPC .............. *A61K 8/29* (2013.01); *A61K 8/0245* (2013.01); *A61K 8/27* (2013.01); *A61K 8/365* (2013.01); *A61K 8/585* (2013.01); *A61Q 17/04* (2013.01); *A61K 2800/412* (2013.01); *A61K 2800/413* (2013.01); *A61K 2800/622* (2013.01); *A61K 2800/651* (2013.01)

(58) Field of Classification Search
CPC .......... A61K 8/29; A61K 8/0245; A61K 8/27; A61K 8/365; A61K 8/585; A61K 2800/412; A61K 2800/413; A61K 2800/622; A61K 2800/651; A61Q 17/04
See application file for complete search history.

(56) References Cited

U.S. PATENT DOCUMENTS 9,254,398 B2  2/2016  Schlossman
2005/0008587 A1  1/2005  Schulz et al.
2009/0291107 A1  11/2009  Schehlmann
2011/0111957 A1* 5/2011  Ishaque .................. A01N 25/22
                                                                                  424/490
2016/0158132 A1  6/2016  Herzog et al.

FOREIGN PATENT DOCUMENTS

| EP | 3 162 359 A1 | 5/2017 | |
| EP | 3678633 B1 | 1/2022 | |
| JP | 2012-521442 A | 9/2012 | |
| JP | 2017-7888 A | 1/2017 | |
| JP | 2017-137300 A | 8/2017 | |
| WO | WO 2014/010101 A1 | 1/2014 | |
| WO | WO-2014195872 A1 * | 12/2014 | ............. A01N 25/12 |
| WO | WO 2015/188335 A1 | 12/2015 | |
| WO | WO 2017/083118 | 5/2017 | |

OTHER PUBLICATIONS

ChemIDplus, Triethoxycaprylylsilane, 2022, National Library of Medicine; from https://chem.nlm.nih.gov/chemidplus/rn/2943-75-1 (Year: 2022).*
EP 18 85 3150.3, Decision to Grant a European Patent, dated Dec. 9, 2021, 2 pages—English.
JP 2020-514250, Notice of Reasons for Rejection, dated Nov. 12, 2021, 2 pages—Japanese, 2 pages—English.
EP 18 85 3150, Extended European Search Report, dated May 7, 2021, 5 pages—English.
JP 2020-513250, Japanese Office Action dated Mar. 18, 2021, 4 pages—Japanese, 8 pages—English.
German Patent No. 112018004752.0, Search Report dated Aug. 31, 2020, 4 pages—English, 7 pages—German.
PCT/US2018/049035, International Search Report and Written Opinion dated Dec. 20, 2018, 6 pages—English.
EP 18 85 3150.3, Intent to Grant dated Nov. 12, 2021, 5 pages—English.
EP 18 85 3150.3, Bibliographic Data, 2 pages—English.
EP 18 85 3150.3, Amended Specification—27 pages—English.
Brazil Pat. No. BR 112020004370-2 issued Aug. 30, 2022, 36 pages—Spanish, 1 page—English abstract.
Japanese Patent Appln. Serial No. JP 2020-514250, Decision to Grant dated May 10, 2022, 2 pages—Japanese; 2 page—English.
CN 201880057815.X, Chinese First Office Action dated Mar. 18, 2022, 2 pages—Chinese, 2 pages—English.
CN 20180057815.X, Chinese First Office Action text dated Mar. 18, 2022, 1 page—Chinese.
PCT/18/49035 filed Aug. 31, 2018.
U.S. Appl. No. 62/554,069, filed Sep. 15, 2017.
CN 201880057815.X, Observation dated Nov. 7, 2022, 2 pages—Chinese, 2 pages Emglish.
Amended Claims dated Nov. 7, 2022, 2 pages—Chinese, 2 pages—English.

* cited by examiner

*Primary Examiner* — Bethany P Barham
*Assistant Examiner* — Ayaan A Alam
(74) *Attorney, Agent, or Firm* — Andrew F. Young; Nolte Lackenbach Siegel

(57) ABSTRACT

Ultraviolet radiation sun protective compositions are reported which feature micronized metal oxide inorganic particles selected from zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4.

16 Claims, No Drawings

HYDROXY CINNAMATE AND SILANOL ADDUCT COATED INORGANIC SUNSCREEN AGENTS

CROSS REFERENCE TO RELATED APPLICATIONS

This application relates to, and claims priority from, WIPO Ser. No. PCT/US2018/049035 filed Aug. 31, 2018, the entire contents of which are incorporated herein by reference, which in turn claims priority from U.S. Ser. No. 62/554,069 filed Sep. 5, 2017, the entire contents of which are incorporated herein by reference.

FIGURE SELECTED FOR PUBLICATION

None

BACKGROUND OF THE INVENTION

Field of the Invention

The invention relates to inorganic metal oxide particles useful as sunscreen agent components for skin and personal care compositions.

Description of the Related Art

Sunlight can be seriously damaging to human skin and destructive to hair. Ultraviolet segments of sunlight are known to accelerate photo aging of the human dermis. Acute exposure may even cause painful erythema. For these reasons, cosmetic chemists often combine organic sunscreen agents into their formulations. The spectrum of UVA and UVB radiation ordinarily is addressed by cocktails of two or more organic sunscreen agents.

Unfortunately, organic type sunscreen agents suffer from certain problems. Under the bombardment of ultraviolet radiation, the organic sunscreens themselves degrade. Photostability may last for only a few hours. Consumers thinking that they are fully protected with their sunscreen lotion, often expose themselves for a time beyond the photostability limit. A second problem is that prominent organic sunscreen agents under certain conditions are prone to cause skin irritation.

In recent times, microfine zinc oxide and microfine titanium oxide have been shown to deflect ultraviolet radiation of both UVA and UVB type. No longer is photostability and skin irritation a problem. But with any new technology, issues do arise. One problem is formulation space. There is a limit to how much metal oxide particles can be suspended within a sunscreen or personal care composition. Ways are needed to raise the sun protective factor (SPF) while keeping constant the level of metal oxide particles.

Background literature includes the following disclosures. U.S. Pat. No. 5,587,148 (Mitchell and Mitchnik) discloses as sunscreen agent a dispersion of micronized particles of zinc oxide with diameter of less than 0.2 micron (200 nm).

U.S. Pat. No. 8,623,386 B2 (Schlossman et al) describes coated metal oxide particles used as pigments in cosmetic compositions. These particles are reported available in primary particle size less than 200 nm and also as pigmentary grade with sizes larger than 200 nm. Coatings are preferably jojoba ester but may also be selected from soya wax, candililla wax, castor oil, coconut oil, macadamia nut oil, and even many fractions of mineral oil.

U.S. Pat. No. 9,254,398 (Schlossman et al) discloses a series of two-layer coated micronized metal oxide powders with good self-dispersibility. These are intended as ingredients for cosmetic products such as makeup, lipstick, nail enamel, eye shadow and mascara. The first of the two layers is triethoxycaprylylsilane. The second, an outer coating, is polyhydroxystearic acid.

ASPECTS AND SUMMARY OF THE INVENTION

Ultraviolet radiation sun protective compositions are reported which feature micronized metal oxide inorganic particles selected from the group consisting of zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4.

Further provided are cosmetic products based upon:

(i) ultraviolet radiation sun protective compositions including micronized metal oxide inorganic particles selected from the group consisting of zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4; and (ii) a dermatologically acceptable carrier supporting the ultraviolet radiation sun protective compositions, the compositions being present in the carrier in a relative weight ratio of 1:100 to 1:4.

Still further provided is a method for producing ultraviolet radiation protective compositions which include the steps of:

(i) providing in powdered form micronized metal oxide inorganic particles selected from the group consisting of zinc oxide, titanium dioxide and mixtures thereof;

(ii) preparing a coating adduct by providing a silanol and mixing the silanol with a hydroxy cinnamate; and (iii) combining in a vessel the adduct with the powdered form of the micronized metal oxide inorganic particles to create inorganic particles surrounded by a coating of the adduct, amounts of the adduct to the inorganic particles being in a relative weight ratio of 1:200 to 1:4; and (iv) discharging coated particles from the vessel.

According to another alternative aspect of the present invention, there is provided a ultraviolet radiation sun protective composition, comprising: micronized metal oxide inorganic particles selected from the group consisting of zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4, including every ratio between this range, for example at ratios of 1:199, 1:198 . . . to . . . 1:5, 1:4.

According to another alternative aspect of the present invention, there is provided a ultraviolet radiation sun protective composition, wherein: the hydroxy cinnamate is a C1-C8 ester of an acid selected from the group consisting of ferulic acid, caffeic acid and chlorogenic acid.

According to another alternative aspect of the present invention, there is provided a ultraviolet radiation sun protective composition, wherein: the C1-C8 ester is selected from the group consisting of methyl, ethyl, propyl, isopropyl and mixtures thereof.

According to another alternative aspect of the present invention, there is provided a ultraviolet radiation sun protective composition, wherein: the hydroxy cinnamate in acid form is selected from the group consisting of ferulic acid, caffeic acid and chlororgenic acid.

According to another alternative aspect of the present invention, there is provided a ultraviolet radiation sun protective composition, wherein: the adduct to inorganic particles are present in a relative weight ratio of 1:100 to 1:10, including every ratio between this range, for example at ratios of 1:99, 1:98 . . . to . . . 1:11, 1:10.

According to another alternative aspect of the present invention, there is provided a ultraviolet radiation sun protective composition, wherein: the inorganic particles have a primary particle size ranging from 5 to 150 nm, including every particle size between this range, for example sizes 5.5 nm . . . to . . . 148 nm, 149 nm, and 150 nm.

According to another alternative aspect of the present invention, there is provided a ultraviolet radiation sun protective composition, wherein: the relative weight ratio of the hydroxy cinnamate to the silanol is present in a relative weight ratio ranging from 1:20 to 20:1, including every ratio between this range, for example at ratios of 1:19, 1:18 . . . to . . . 19:1, 20:1.

According to another alternative aspect of the present invention, there is provided a ultraviolet radiation sun protective composition, wherein: the silanol comprises C1-C20 acyl, alkyl or phenyl units which units may number from one to three and bond directly to silicon, and from one to three hydroxyl or C1-3 alkoxy units which may bond directly to the silicon.

According to another alternative aspect of the present invention, there is provided a ultraviolet radiation sun protective composition, wherein: the C1-C20 alkyl is selected from the group consisting of methyl, ethyl, isopropyl, hexyl, heptyl, octyl, decyl, lauryl, monohydroxyoctyl, dihydroxyoctyl and combinations thereof.

According to another alternative aspect of the present invention, there is provided a ultraviolet radiation sun protective composition, wherein: the C1-C20 acyl radical is capryl.

According to another alternative aspect of the present invention, there is provided a ultraviolet radiation sun protective composition, wherein: the silanol is a silsesquioxane.

According to another alternative aspect of the present invention, there is provided a cosmetic product, comprising: (i) ultraviolet radiation sun protective compositions comprising micronized metal oxide inorganic particles selected from the group consisting of zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4, including every ratio between this range; and (ii) a dermatologically acceptable carrier supporting the ultraviolet radiation sun protective composition, the composition being present in the carrier in a relative weight ratio of 1:100 to 1:4, including every ratio between this range, for example at ratios of 1:99, 1:98 . . . to . . . 1:5, 1:4.

According to another alternative aspect of the present invention, there is provided a cosmetic product, wherein: the carrier is selected from the group consisting of water, emollients, fatty acids, fatty alcohols, humectants, thickeners and mixtures thereof.

According to another alternative aspect of the present invention, there is provided a cosmetic product, wherein: the coated ultraviolet sun protective composition to the carrier is present in a relative weight ratio of 1:50 to 1:1.5, including every ratio between this range, for example at ratios of 1:49, 1:48 . . . to . . . 1:1.6, 1:1.5.

According to another alternative aspect of the present invention, there is provided a cosmetic product, wherein: the carrier is present in an amount from 1 to 99.9% by weight of the cosmetic product, including present in any amount between that range from 1% . . . to 99.9%.

According to another alternative aspect of the present invention, there is provided a cosmetic product, further comprising: organic sunscreens selected from the group consisting of 2-ethylhexyl p-methoxycinnamate, 4,4'-t-butyl methoxydibenzoylmethane, octylsalicylate, tetraphthalylidene dicamphor sulfonic acid, benzophenone-3 and mixtures thereof.

According to another alternative aspect of the present invention, there is provided a method for producing ultraviolet radiation protective compositions, comprising the steps of: (i) providing in powdered form micronized metal oxide inorganic particles selected from the group consisting of zinc oxide, titanium dioxide and mixtures thereof; (ii) preparing a coating adduct by providing a silanol and reacting the silanol with a hydroxy cinnamate; (iii) combining in a vessel the adduct with the powdered form of the micronized metal oxide inorganic particles to create inorganic particles surrounded by a coating of the adduct, amounts of the adduct to the inorganic particles being in a relative weight ratio of 1:200 to 1:4; and (iv) discharging coated particles from the vessel.

The above and other aspects, features and advantages of the present invention will become apparent from the following description read in conjunction with the accompanying tables.

BRIEF DESCRIPTION OF THE DRAWINGS

None

DETAILED DESCRIPTION OF THE INVENTION

We have found that the SPF of compositions formulated with micronized metal oxide inorganic particles can be enhanced by coating the inorganic particles with an adduct formed between a hydroxy cinnamate and a silanol.

Relative weight ratio of the adduct to the metal oxide may range from 1:200 to 1:4, especially from 1:100 to 1:10, more especially from 1:50 to 1:30 by weight. When placed within a cosmetic product having a carrier, the relative weight ratio of the coated ultraviolet radiation sun protective compositions to the carrier may range from 1:100 to 1:4, especially from 1:50 to 1:5.

Effective adduct coating methods for use herein include (1) high speed milling, (2) supercritical carbon dioxide processing and (3) solvent slurry application with subsequent solvent removal.

Metal Oxide Inorganic Particles

Micronized zinc oxide, titanium dioxide and mixtures thereof are the most suitable metal oxides. The term 'micronized' means metal oxides having a primary particles size ranging from 5 to 150 nm if the particles are spherical or granular. If the particles are acicular, the primary particle size may range from 5 to 50 nm by 50 to 150 nm. Primary particle size may be analyzed using Transmission Electron Microscopy.

Adduct

A first component of the adduct is a hydroxy cinnamate in acid or ester form. The ester may be a C1-C8 alkyl ester selected from the group consisting of methyl, ethyl, propyl, isopropyl, phenyl and mixtures thereof. Most useful ester cinnamates are ethyl ferulate, methyl ferulate, caffeic acid methyl ester, caffeic acid phenethyl ester and caffeic acid ethyl ester. The preferred acids are ferulic acid, chlorogenic acid and caffeic acid. Precursor materials to the hydroxy cinnamate such as 7-hydroxycoumarin may also be effective.

A second component of the adduct is a silanol. Suitable silanols include those with C1-C20 alkyl and/or phenyl units which units may number from one to three, but advantageously can be a single alkyl or phenyl radical. The term 'alkyl' and 'phenyl' may include radicals with one or more hydroxyl, methoxy, ethoxy, propoxy and combination thereof substituents. Suitable but not limiting C1-C20 alkyls may be selected from the group consisting of methyl, ethyl, isopropyl, hexyl, heptyl, octyl, decyl, lauryl, monohydroxyoctyl, dihydroxyoctyl, C1-20 acyl and combinations thereof. Most preferred is the acyl radical octanoyl (also known as capryl).

The silanol may also have from one to three hydroxyl substituents. Advantageously, the silanol may have three hydroxyls forming a silane triol. Silanols may be generated by hydrolysis of silane alkoxy groups. For instance, triethoxycaprylylsilane upon de-ethoxylation/hydrolysis generates caprylylsilanetriol.

Silsesquioxanes may be suitable as a silanol. Silsesquioxanes are organosilicon compounds with the formula $[RSiO_{3/2}]_n$ wherein R=H, alkyl, aryl or alkoxy). These silanols adopt cage-like or polymeric structures with Si—O—Si linkages and tetrahedral Si vertices. Silsesquioxanes are members of polyoctahedral silsesquioxanes ("POSS"), an example of which is TrisilanoiPhenyl POSS.

Relative weight ratio of the hydroxy cinnamate to the silanol may range from 1:20 to 20:1, especially from 1:5 to 5:1, more especially from 1:2 to 2:1, and particularly 1:1.

Cosmetic Products

Cosmetic products formulated with the improved coated metal oxide sun protective particles usually include a dermatologically acceptable carrier. Amounts of the carrier may range from 1 to 99.9%, preferably from 70 to 95%, optimally from 80 to 90% by weight of the product. Among the useful carriers are water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from 5 to 98%, preferably 20 to 70%, optimally from 35 to 60% by weight.

Water when present as carrier or otherwise may advantageously be incorporated into the compositions as a deionized, sterilized or pasteurized liquid or can be heat treated or irradiated after having been mixed with other components of the composition. These treatments insure elimination of pathogenic microbes.

Emollient materials may serve as dermatologically acceptable carriers. These may be in the form of silicone oils, synthetic or natural esters and hydrocarbons. Amounts of the emollients may range anywhere from 0.1 to 95%, preferably between 1 and 50% by weight of the cosmetic product.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a. Alkyl esters of saturated fatty acids having 10 to 24 carbon atoms. Examples thereof include behenyl neopentanoate, isononyl isonanonoate, isopropyl myristate and octyl stearate.
b. Ether-esters such as fatty acid esters of ethoxylated saturated fatty alcohols.
c. Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl gly col esters of $C_1$-$C_{30}$ alcohols.
d. Wax esters such as beeswax, spermaceti wax and tribehenin wax.
e. Sugar ester of fatty acids such as sucrose polybehenate and sucrose polycottonseedate.

Hydrocarbons which are suitable carriers include petrolatum, mineral oil, $C_{11}$-$C_{13}$ isoparaffins, and especially isohexadecane, available commercially as Permethyl 101A from Presperse Inc.

Fatty acids having from 10 to 30 carbon atoms may also be suitable as carriers. Illustrative of this category are pelargonic, lauric, myristic, palmitic, stearic, isostearic, oleic, and behenic acids.

Fatty alcohols having from 10 to 30 carbon atoms are another useful category of carrier. Illustrative of this category are stearyl alcohol, lauryl alcohol, myristyl alcohol and cetyl alcohol.

Humectants of the polyhydric alcohol-type can be employed as carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the product.

Thickeners can be utilized as part of the dermatologically acceptable carriers. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums may be suitable thickeners and can include guar, xanthan, sclerotium, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight of the product.

Cosmetic products intended to be skin tighteners normally will be formulated with a skin lightening compound. Illustrative substances are placental extract, lactic acid, niacinamide, arbutin, kojic acid, ferulic acid, hydroquinone, resorcinol and derivatives including 4-substituted resorcinols and combinations thereof. Amounts of these substances may range from 0.1 to 10%, preferably from 0.5 to 2% by weight of the product.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides are useful. Amounts of these materials may range from 0.000001 to 10%, preferably from 0.0001 to 1% by weight of the composition.

Cosmetic compositions may include vitamins. Illustrative vitamins are Vitamin A (retinol), Vitamin $B_2$, Vitamin $B_3$ (niacinamide), Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10% by weight of the composition.

The cosmetic compositions may be formulated into a wide variety of product types that include but are not limited to solutions, suspensions, lotions, creams, gels, toners, sticks, sprays, ointments, cleansing liquid washes and solid bars, shampoos and hair conditioners, hair colorants, pastes, foams, powders, mousses, wipes, hydrogels, film-forming products, facial and skin masks, make-up such as foundations, lipsticks, eye liners, and eye shadows, and the like.

Additional sun protection may utilize organic sunscreens. They include both UVA and UVB protective ranges. Organic sunscreens will have at least one chromophoric group absorbing within the ultraviolet ranging from 290 to 400 nm. Chromophoric organic sunscreens may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly important sunscreens are: 2-ethylhexyl p-methoxycinnamate (available as Parsol MCX®), 4,4'-t-butyl methoxydibenzoylmethane (known commonly as Avobenzone, available as Parsol 17890), octylsalicylate (available as Dermablock OS®), tetraphthalylidene dicamphor sulfonic acid (available as Mexoryl SX®), benzophenone-3 (Oxybenzone) and mixtures Amounts of organic sunscreen may range from 0.01 to 20%, usually from 0.5 to 15%, and often from 4 to 12% by weight of the cosmetic composition.

Surfactants suitable for use may be those which can form emulsions and/or association structures. Surfactants can be categorized as being of the anionic, nonionic, cationic, or amphoteric type. The term "surfactants" are defined herein to include materials otherwise called "emulsifiers".

Examples of surfactants which may be used in the compositions described herein include salts of C8-C22 alkyl chain compounds. Representative are sodium tallowate, sodium cocoate, sodium alkyl sulfate (e.g., sodium lauryl sulfate and sodium myristyl sulfate), sodium N-acyl sarcosinates (e.g., sodium N-lauroyl sarcosinate and sodium N-myristoyl sarcosinate), sodium dodecylbenzenesulfonate, sodium hydrogenated coconut fatty acid monoglyceride sulfate, sodium lauryl sulfoacetate and N-acyl glutamates (e.g., N-palmitoyl glutamate), N-methylacyltaurin sodium salt, N-methylacylalanine sodium salt, sodium alpha-olefin sulfonate and sodium dioctylsulfosuccinate; N-alkylaminoglycerols (e.g., N-lauryl-diamino-ethylglycerol and N-myristyldiaminoethyl glycerol), N-alkyl-N-carboxymethylammonium betaine and sodium 2-alkyl-1-hydroxyethylimidazoline betaine; polyoxyethylenealkyl ether, polyoxyethylene alkylaryl ether, polyoxyethylene lanolin alcohol, polyoxyethylene glyceryl monoaliphatic acid ester, polyoxyethylene sorbitol aliphatic acid ester, polyoxyethylene aliphatic acid ester, higher aliphatic acid glycerol ester, sorbitan aliphatic acid ester, and polyoxyethylenesorbitan aliphatic acid esters such as polyoxyethylenesorbitan monooleate and polyoxyethylene sorbitan monolaurate.

The surfactants can be used at levels from 0.1% to 97%, preferably from 2% to 75%, more preferably from 10% to 90% and most preferably from 20% to 70% by weight of the cosmetic composition.

Preservatives may be incorporated into the cosmetic compositions to protect against the growth of potentially harmful microorganisms. Suitable traditional preservatives are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methylchloroisothiazolinone and methylisothiazolinone combinations, phenoxyethanol, methyl paraben, propyl paraben, imidazolidinyl urea, sodium dehydroacetate and benzyl alcohol. Preservatives may be employed in amounts ranging from 0.01% to 2% by weight of the cosmetic composition.

Desquamation agents may be present. Illustrative are the monocarboxylic acids. Monocarboxylic acids may be substituted or unsubstituted with a carbon chain length of up to 16. Particularly preferred carboxylic acids are the alpha-hydroxycarboxylic acids, beta-hydroxycarboxylic or poly-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic, malic and tartaric acids. A representative salt that is particularly preferred is ammonium lactate. Salicylic acid is representative of the beta-hydroxycarboxylic acids. Amounts of these materials when present may range from 0.01 to 15% by weight of the cosmetic composition.

Preferred desquamation agents may be selected from the group consisting of glycolic acid, lactic acid, salicylic acid, retinoic acid, retinol and mixtures thereof, and including salt forms thereof.

Colorants may either be dyes or pigments. A distinction is usually made between a pigment, which is insoluble in its vehicle (resulting in a suspension), and a dye, which either is itself a liquid or is soluble in its vehicle (resulting in a solution). A colorant can act as either a pigment or a dye depending on the vehicle involved. In some cases, a pigment can be manufactured from a dye by precipitating a soluble dye with a metallic salt. The resulting pigment is called a lake pigment.

Among the more common dyes are Alizarin, Azophloxin, Chrysoidin, Congo Red, Fuchsin acid, Gentian violet, Janus green, Methyl Red, Naphthol Green, Naphthol Yellow, Rose Bengal, Sudan II, Titan Yellow and combinations thereof. Amongst pigments, titanium dioxide and aluminum lakes (aluminum salts of dyes) are most common. Amounts of the colorant may, according to the type of cosmetic product (lipstick, foundation, hair dye, etc) range from 0.000001 to 10%, usually from 0.01 to 5% by weight of the cosmetic composition.

The sun protection factor (SPF rating) has been used to qualitatively describe differences in protective efficacy. SPF is a measure of the fraction of sunburn-producing UV rays that reach the skin. For example, "SPF 15" means that ¹/₁₅th of the burning radiation will reach the skin, assuming sunscreen is applied evenly at a thick dosage of 2 milligrams per square centimeter ($mg/cm^2$). A user can determine the effectiveness of a sunscreen by multiplying the SPF factor by the length of time it takes for him or her to suffer a burn without sunscreen. Thus, if a person develops a sunburn in 10 minutes when not wearing a sunscreen, the same person in the same intensity of sunlight will avoid sunburn for 150 minutes if wearing a sunscreen with an SPF of 15.

Besides an in vivo measurement, SPF can also be measured in vitro with the help of a specially designed spectrometer. In this case, the actual transmittance of the sunscreen is measured, along with the degradation of the product due to being exposed to sunlight. Transmittance of the sunscreen must be measured over all wavelengths in sunlight's UVB-UVA range (290-400 nm), along with a table of how effective various wavelengths are in causing sunburn (the erythemal action spectrum) and the standard intensity spectrum of sunlight. Evaluations of SPF in the Examples which follow report results by the in vitro method.

Except in the examples, or where otherwise explicitly indicated, all numbers in this description indicating amounts of material or conditions of reaction, physical properties of materials and/or use are to be understood as modified by the word "about." All amounts are by weight of the compositions, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Product" as used herein, is meant to include a formulated cosmetic composition used in personal care or cleansing for topical application to skin or hair of mammals, especially humans or for deposition onto textiles. These compositions may be wash-off or leave-on formulations.

EXAMPLE I

Preparation of the adducts and thereupon coating of the zinc oxide and titanium dioxide particles were done in the following manner. The metal oxide was added to a tank with a high speed mixer and mixed for a few minutes to de-agglomerate. In a separate vessel, triethoxycaprylylsilane and ethyl ferulate were mixed together in an isopropanol solvent forming an adduct in solution. Next the solution was sprayed onto the de-agglomerated metal oxide while the latter was being mixed at high speed. Thereafter, mixing was continued for 15 minutes to totally disperse the adduct over the metal oxide particles.

A set of five compositions were formulated incorporating zinc oxide (coated and uncoated) to evaluate SPF performance. Components are outlined within Table I.

TABLE I

| | | Sample Number | | | | |
|---|---|---|---|---|---|---|
| Phase | Ingredient | 1 | 2 | 3 | 4 | 5 |
| A | ZnO (coated and uncoated) | 10.0 | 10.4 | 10.6 | 10.2 | 10.6 |
| A | Tricaprylin | 33.7 | 33.3 | 33.1 | 33.1 | 33.1 |
| A | Polyglyceryl-3 polyricinoleate | 2.0 | 2.0 | 2.0 | 2.0 | 2.0 |
| A | Isododecane | 7.8 | 7.8 | 7.8 | 7.8 | 7.8 |
| B | Quaternium-90 Bentonite | 2.6 | 2.6 | 2.6 | 2.6 | 2.6 |
| C | Polyglyceryl-3 diisostearate | 1.3 | 1.3 | 1.3 | 1.3 | 1.3 |
| C | Cetyl PEG/PPG-10/1 Dimethicone | 1.3 | 1.3 | 1.3 | 1.3 | 1.3 |
| D | Water | 39.5 | 39.5 | 39.5 | 39.5 | 39.5 |
| D | Magnesium Sulphate | 1.5 | 1.5 | 1.5 | 1.5 | 1.5 |
| D | Potassium Sorbate | 0.3 | 0.3 | 0.3 | 0.3 | 0.3 |
| | | 100.0 | 100.0 | 100.0 | 100.0 | 100.0 |

Samples 1-5 were prepared by combining components listed under phase A. The components were subjected to mixing in a homogenizer for 30 minutes at room temperature. Phase B was added to phase A and together were further homogenized for 20 minutes. Thereupon, phase C was added and mixing continued for another 10 minutes.

Components of phase D were charged to a separate vessel and mixed for 5 minutes. Phase D was then added to the combined phases A, B and C while continuing homogenization mixing for 10 minutes.

Another set of four compositions were formulated incorporating titanium dioxide (coated and uncoated) to evaluate SPF performance. Components are outlined within Table II. Preparation of samples 6-9 was similar to that reported above for samples 1-5.

TABLE II

| | | Sample Number | | | |
|---|---|---|---|---|---|
| Phase | Ingredient | 6 | 7 | 8 | 9 |
| A | TiO2 (coated and uncoated) | 5.0 | 5.4 | 5.6 | 5.2 |
| A | Tricaprylin | 38.7 | 38.3 | 38.1 | 38.5 |
| A | Polyglyceryl-3 polyricinoleate | 2.0 | 2.0 | 2.0 | 2.0 |
| A | Isododecane | 7.8 | 7.8 | 7.8 | 7.8 |
| B | Quaternium-90 Bentonite | 2.6 | 2.6 | 2.6 | 2.6 |
| C | Polyglyceryl-3 diisostearate | 1.3 | 1.3 | 1.3 | 1.3 |
| C | Cetyl PEG/PPG-10/1 Dimethicone | 1.3 | 1.3 | 1.3 | 1.3 |
| D | Water | 39.5 | 39.5 | 39.5 | 39.5 |
| D | Magnesium Sulphate | 1.5 | 1.5 | 1.5 | 1.5 |
| D | Potassium Sorbate | 0.3 | 0.3 | 0.3 | 0.3 |
| | | 100.0 | 100.0 | 100.0 | 100.0 |

EXAMPLE II

Performance data is recorded in Table III below. Sample 1 reveals that uncoated zinc oxide at 10% loading has an SPF of 13. Samples 2 and 4 respectively formulated with coatings of triethoxycaprylylsilane and ethyl ferulate exhibit SPF values of 17 and 13.6. These results hardly improve over uncoated zinc oxide. Samples 3 and 5 wherein triethoxycaprylylsilane and ethyl ferulate or ferulic acid have been added as a premix coating adduct reach SPF values of 33 and 24. These SPF values close to triple and double those for uncoated zinc oxide.

SPF performance data with micronized titanium dioxide gives comparable results. Sample 8 with an SPF of 30 for the combined adduct of triethoxycaprylylsilane with ethyl ferulate is substantially higher than the uncoated oxide (Sample 6) or the separate silanol and ferulate coatings (Samples 7 and 9).

TABLE III

| Material | Coating | Sample No. | Amount used % | SPF |
|---|---|---|---|---|
| ZnO (100%) | No coating | 1 | 10.0 | 13 |
| ZnO (96%) | Triethoxycaprylylsilane (4%) | 2 | 10.4 | 17 |
| ZnO (94%) | Triethoxycaprylylsilane (4%) and Ethyl Ferulate (2%) | 3 | 10.6 | 33 |
| ZnO (98%) | Ethyl Ferulate (2%) | 4 | 10.2 | 13.6 |
| ZnO (98%) | Triethoxycaprylylsilane (4%) and Ferulic Acid (2%) | 5 | 10.6 | 24 |
| TiO2 (100%) | No Coating | 6 | 5.0 | 20 |
| TiO2 (96%) | Triethoxycaprylylsilane (4%) | 7 | 5.4 | 20 |
| TiO2 (94%) | Triethoxycaprylylsilane Ethyl Ferulate (2%) | 8 | 5.6 | 30 |
| TiO2 (98%) | Ethyl Ferulate (2%) | 9 | 5.2 | 20 |

*Note:
Isopropanol employed as carrier in all samples

Sample 1 as reported under Example 1 was used as a base formula to assess the SPF effect of various ratios of ethyl ferulate and triethoxycaprylylsilane coating of zinc oxide. The ethyl ferulate and triethoxycaprylylsilane amounts coated over zinc oxide are reported under Table IV. Table V reports the SPF results. Apparently ethyl ferulate and triethoxycaprylylsilane are mutually SPF interactive over a broad range of relative amounts.

TABLE IV

| | 1 | 2 | 3 | 4 | 5 |
|---|---|---|---|---|---|
| Ethyl Ferulate (%) | 2.0 | 3.0 | 3.0 | 4.0 | 4.0 |
| Triethoxycaprylylsilane (%) | 2.0 | 2.0 | 1.0 | 1.0 | 0.5 |
| Zinc Oxide (%) | 96.0 | 95.0 | 96.0 | 95.0 | 95.5 |

TABLE V

| | 1 | 2 | 3 | 4 | 5 |
|---|---|---|---|---|---|
| Use level of coated ZnO* (%) | 10.6 | 10.7 | 10.6 | 10.7 | 10.7 |
| SPF | 23 | 23 | 19 | 20 | 18 |

*Use level adjusted to 10.2% Zinc Oxide.

EXAMPLE III

Adduct coated ZnO can be used to make sunscreen formulations of various types but not limited to: W/O; O/W; pickering emulsions; anhydrous; alcohol-based suspension. The adduct is an interesterification of ethyl ferulate with triethoxy silanol. Illustrative cosmetic product formulations are described below.

| W/O Emulsion | | | | | | |
|---|---|---|---|---|---|---|
| Phase | Ingredient | 1 | 2 | 3 | 4 | 5 |
| A | Adduct Coated ZnO | 30.0 | 1.0 | 5.0 | 10.0 | 20.0 |
| A | Tricaprylin | 24.8 | 32.7 | 29.8 | 28.8 | 25.3 |
| A | Isododecane | 7.8 | 8.9 | 7.8 | 7.8 | 7.8 |
| B | Quaternium-90 Bentonite | 2.6 | 2.6 | 2.6 | 2.6 | 2.6 |
| | Propylene Carbonate | 1.0 | 1.0 | 1.0 | 1.0 | 1.0 |
| C | Cetyl PEG/PPG-10/1 Dimethicone | 2.0 | 2.0 | 2.0 | 2.0 | 2.0 |
| D | Water | 30.0 | 50.0 | 50.0 | 46.0 | 39.5 |
| D | Magnesium Sulphate | 1.5 | 1.5 | 1.5 | 1.5 | 1.5 |
| D | Potassium Sorbate | 0.3 | 0.3 | 0.3 | 0.3 | 0.3 |
| | | 100.0 | 100.0 | 100.0 | 100.0 | 100.0 |

| O/W Emulsion | | | | |
|---|---|---|---|---|
| Phase | Ingredient | 1 | 2 | 3 |
| A | Water | 59.3 | 54.3 | 49.3 |
| A | Glycerin | 3.0 | 3.0 | 3.0 |
| A | Potassium Sorbate | 0.30 | 0.30 | 0.30 |
| B | Adduct Coated ZnO | 5.0 | 10.0 | 15.0 |
| B | Tricaprylin | 20.0 | 20.0 | 20.0 |
| B | Isododecane | 7.8 | 7.8 | 7.8 |
| B | Arlacel ® 165 | 2.6 | 2.6 | 2.6 |
| C | Aristoflex AVC ® | 1.0 | 1.0 | 1.0 |
| D | Phenoxyethanol | 1.0 | 1.0 | 1.0 |
| | | 100.0 | 100.0 | 100.0 |

EXAMPLE IV

Adduct (ethyl ferulate/triethoxycaprylylsilane) coated titanium dioxide can be used to make sunscreen formulations of various types but not limited to: W/O; O/W; pickering emulsions; anhydrous; alcohol-based suspension. Illustrative cosmetic product formulations are described below.

W/O Emulsion

| Phase | Ingredient | 1 | 2 | 3 | 4 | 5 |
|---|---|---|---|---|---|---|
| A | Adduct Coated TiO2 | 30.0 | 1.0 | 5.0 | 10.0 | 20.0 |
| A | Tricaprylin | 24.8 | 32.7 | 29.8 | 28.8 | 25.3 |
| A | Isododecane | 7.8 | 8.9 | 7.8 | 7.8 | 7.8 |
| B | Quaternium-90 Bentonite | 2.6 | 2.6 | 2.6 | 2.6 | 2.6 |
|   | Propylene Carbonate | 1.0 | 1.0 | 1.0 | 1.0 | 1.0 |
| C | Cetyl PEG/PPG-10/1 Dimethicone | 2.0 | 2.0 | 2.0 | 2.0 | 2.0 |
| D | Water | 30.0 | 50.0 | 50.0 | 46.0 | 39.5 |
| D | Magnesium Sulphate | 1.5 | 1.5 | 1.5 | 1.5 | 1.5 |
| D | Potassium Sorbate | 0.3 | 0.3 | 0.3 | 0.3 | 0.3 |
|   |   | 100.0 | 100.0 | 100.0 | 100.0 | 100.0 |

O/W Emulsion

| Phase | Ingredient | 1 | 2 | 3 |
|---|---|---|---|---|
| A | Water | 59.3 | 54.3 | 49.3 |
| A | Glycerin | 3.0 | 3.0 | 3.0 |
| A | Potassium Sorbate | 0.30 | 0.30 | 0.30 |
| B | Adduct Coated Titanium Dioxide | 5.0 | 10.0 | 15.0 |
| B | Tricaprylin | 20.0 | 20.0 | 20.0 |
| B | Isododecane | 7.8 | 7.8 | 7.8 |
| B | Arlacel ® 165 | 2.6 | 2.6 | 2.6 |
| C | Aristoflex AVC ® | 1.0 | 1.0 | 1.0 |
| D | Phenoxyethanol | 1.0 | 1.0 | 1.0 |
|   |   | 100.0 | 100.0 | 100.0 |

O/W Emulsion

| Phase | Ingredient | 1 | 2 | 3 |
|---|---|---|---|---|
| A | Water | 59.3 | 54.3 | 49.3 |
| A | Glycerin | 3.0 | 3.0 | 3.0 |
| A | Potassium Sorbate | 0.30 | 0.30 | 0.30 |
| B | Adduct Coated Titanium Dioxide | 5.0 | 10.0 | 15.0 |
| B | Tricaprylin | 15.0 | 15.0 | 15.0 |
| B | Benzophenone-3 | 3.0 | 3.0 | 3.0 |
| B | Isododecane | 7.8 | 7.8 | 7.8 |
| B | Arlacel ® 165 | 2.6 | 2.6 | 2.6 |
| C | Aristoflex AVC ® | 1.0 | 1.0 | 1.0 |
| D | Phenoxyethanol | 1.0 | 1.0 | 1.0 |
|   |   | 100.0 | 100.0 | 100.0 |

While the present compositions and methods have been described with reference to the specific variations thereof, it should be understood by those skilled in the art that various changes may be made and equivalents may be substituted without departing from the true spirit and scope of the compositions and methods described herein. In addition, many modifications may be made to adapt a particular situation, material, composition of matter, process, process step or steps, to the objective, spirit and scope of the compounds and methods described herein. All patents and publications cited above are hereby incorporated by reference.

What is claimed is:

1. An ultraviolet radiation sun protective composition, comprising: micronized metal oxide inorganic particles selected from the group consisting of zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4.

2. The composition according to claim 1, wherein: the hydroxy cinnamate is a C1-C8 ester of an acid selected from the group consisting of ferulic acid, caffeic acid and chlorogenic acid.

3. The composition according to claim 2, wherein: the C1-C8 ester is selected from the group consisting of methyl, ethyl, propyl, isopropyl and mixtures thereof.

4. The composition according to claim 1, wherein: the hydroxy cinnamate in acid form is selected from the group consisting of ferulic acid, caffeic acid and chlorogenic acid.

5. The composition according to claim 1, wherein: the adduct to inorganic particles are present in a relative weight ratio of 1:100 to 1:10.

6. The composition according to claim 1, wherein: the inorganic particles have a primary particle size ranging from 5 to 150 nm.

7. The composition according to claim 1, wherein: the relative weight ratio of the hydroxy cinnamate to the silanol is present in a relative weight ratio ranging from 1:20 to 20:1.

8. The composition according to claim 1, wherein: the silanol comprises C1-C20 acyl, alkyl or phenyl units which units may number from one to three and bond directly to silicon, and from one to three hydroxyl or C1-3 alkoxy units which may bond directly to the silicon.

9. The composition according to claim 8, wherein: the C1-C20 alkyl is selected from the group consisting of methyl, ethyl, isopropyl, hexyl, heptyl, octyl, decyl, lauryl, monohydroxyoctyl, dihydroxyoctyl and combinations thereof.

10. The composition according to claim 8, wherein: the C1-C20 acyl radical is capryl.

11. A cosmetic product, comprising:
   (i) ultraviolet radiation sun protective compositions comprising micronized metal oxide inorganic particles selected from the group consisting of zinc oxide, titanium dioxide and mixtures thereof, the inorganic particles being coated with an adduct of a hydroxy cinnamate and a silanol, amounts of the adduct to the inorganic particles being in a relative weight ratio of 1:200 to 1:4; and
   (ii) a dermatologically acceptable carrier supporting the ultraviolet radiation sun protective composition, the composition being present in the carrier in a relative weight ratio of 1:100 to 1:4.

12. The product according to claim 11, wherein: the carrier is selected from the group consisting of water, emollients, fatty acids, fatty alcohols, humectants, thickeners and mixtures thereof.

13. The product according to claim 11, wherein: the coated ultraviolet sun protective composition to the carrier is present in a relative weight ratio of 1:50 to 1:1.5.

14. The product according to claim 11, wherein: the carrier is present in an amount from 1 to 99.9% by weight of the cosmetic product.

15. The product according to claim 11, further comprising: organic sunscreens selected from the group consisting of 2-ethylhexyl p-methoxycinnamate, 4,4'-t-butyl methoxydibenzoylmethane, octylsalicylate, tetraphthalylidene dicamphor sulfonic acid, benzophenone-3 and mixtures thereof.

16. An ultraviolet radiation sun protective composition, comprising: micronized metal oxide inorganic particles selected from the group consisting of zinc oxide, titanium dioxide and mixtures thereof, the inorganic particles being coated with an adduct of ethyl ferulate, and triethoxycaprylylsilane, amounts of the adduct to the inorganic particles being in a relative weight ratio, adduct:inorganic particles, of 1:200 to 1:4.

* * * * *